United States Patent [19]

McGehee et al.

[11] Patent Number: 5,510,521

[45] Date of Patent: Apr. 23, 1996

[54] PROCESS FOR THE PRODUCTION OF AROMATIC CARBOXYLIC ACIDS

[75] Inventors: James F. McGehee; Sunday O. Ogundiran; Robert Lin, all of Kingsport, Tenn.

[73] Assignee: Eastman Chemical Company, Kingsport, Tenn.

[21] Appl. No.: 411,363

[22] Filed: Mar. 27, 1995

[51] Int. Cl.⁶ .................................................. C07C 51/265
[52] U.S. Cl. .......................................... 562/414; 562/413
[58] Field of Search .................................... 562/413, 414

[56] References Cited

U.S. PATENT DOCUMENTS

| | | |
|---|---|---|
| 2,788,367 | 4/1957 | Bills et al. . |
| 2,962,361 | 11/1960 | Spiller, Jr. et al. . |
| 3,047,614 | 7/1962 | Pennington et al. . |
| 3,064,044 | 11/1962 | Baldwin . |
| 3,155,718 | 11/1964 | Brown et al. . |
| 3,215,733 | 11/1965 | MacLean et al. . |
| 3,402,184 | 9/1968 | Berthoux et al. ........................ 260/346 |
| 3,472,630 | 10/1969 | Baldwin et al. . |
| 3,665,033 | 5/1972 | Ohlswager . |
| 3,668,257 | 6/1972 | Schaeffer ............................... 206/604 |
| 3,996,271 | 12/1976 | Yokota et al. . |
| 4,250,330 | 2/1981 | Costantini et al. . |
| 4,405,809 | 9/1983 | Stech et al. ............................. 562/487 |
| 4,777,287 | 10/1988 | Zeitlin et al. . |
| 4,855,492 | 8/1989 | Hundley . |
| 4,863,888 | 9/1989 | Melville et al. . |
| 5,004,830 | 4/1991 | Park et al. ............................... 562/413 |
| 5,087,741 | 2/1992 | Tennant et al. . |
| 5,095,142 | 3/1992 | Janulis . |
| 5,099,064 | 3/1992 | Huber, Jr. et al. . |

*Primary Examiner*—José G. Dees
*Assistant Examiner*—Samuel Barts
*Attorney, Agent, or Firm*—Cheryl J. Tubach; Harry J. Gwinnell

[57] ABSTRACT

Disclosed is an improved process for the continuous production of aromatic carboxylic acids by the liquid-phase oxidation of an alkyl aromatic compound with an oxygen-containing gas in the presence of oxidation catalyst which effectively utilizes the heat of reaction in the process of removing excess water generated from the reaction and minimizes the loss of solvent used as the carrier for the reaction catalyst. Operation of the process is improved by removing reactor off-gas directly into a water removal column for distillation. A portion of distillate condensed from the overhead aqueous vapors of the water removal column is refluxed to the fractionating zone of the water removal column. A bottoms liquid of partially de-watered process solvent obtained from the water removal column is sprayed into the reactor above the phase separation of the gas/liquid contents thereby enriching the water content of the reactor off-gas to improve the efficiency of the water removal column without additional heat input beyond that of the heat of reaction.

6 Claims, 1 Drawing Sheet

PROCESS FOR THE PRODUCTION OF AROMATIC CARBOXYLIC ACIDS

TECHNICAL FIELD

This invention pertains to an improved process for the continuous production of aromatic polycarboxylic acids by the liquid-phase oxidation of alkyl aromatic hydrocarbons with molecular oxygen in the presence of an oxidation catalyst or catalyst system. More particularly, this invention pertains to such oxidation processes carried out in a columnar oxidation reactor provided with means to effectively remove the excess water generated from the process with minimal solvent loss utilizing the energy of oxidation.

BACKGROUND OF THE INVENTION

The liquid-phase oxidation of an alkyl aromatic hydrocarbon to an aromatic carboxylic acid is a highly exothermic reaction commonly carried out in a vented, intimately-mixed, columnar oxidation reactor. The oxidation process comprises continuously feeding separately or in admixture an alkyl aromatic hydrocarbon, fresh and/or recycled solvent generally in aqueous solution, and catalyst components to the reactor to which a molecular oxygen-containing gas also is fed, normally at or near the bottom of the reactor. This process gas rises through the liquid contents of the reactor resulting in vigorous agitation of the reaction mixture and providing intimate contact between the alkyl aromatic hydrocarbon and the process solvent having dissolved therein the catalyst or catalyst components. The aromatic carboxylic acid produced is removed continuously through a lower exit port located at or near the base of the reactor as a slurry in the solvent which also contains soluble catalyst components. After separation of the aromatic carboxylic acid product, the solvent is returned to the reactor.

Oxygen-depleted process gas, along with minor amounts of solvent decomposition products, is removed through an upper exit port located at or near the top of the reactor. The heat of reaction is also removed through the upper exit port by vaporization of the process solvent and water generated by the reaction. The oxygen-depleted process gas and the vaporized process solvent and water comprise the reactor off-gas which is typically condensed by means of one or more condensers to separate the solvent and water for recycling to the reactor. The condensed aqueous solvent may be subjected to a water removal step prior to recycling.

The described production system can be utilized in the manufacture of aromatic carboxylic acids at excellent production rates relative to the volume of the reactor. One significant problem presented by the production system is the efficient removal of the excess water generated by the reaction since the water concentration must be held at an acceptable level, typically below 10 percent, for the reaction to continue at a reasonable rate. The reaction produces one mole of water per mole of carboxyl moiety produced. In addition, there are other side reactions which release water, i.e. the direct oxidation of the solvent to form by-products, and water may be added to the process for other reasons such as scrubbing off-gas for solvent recovery. Typically, water is removed by conventional distillation methods.

Another problem is the effective removal of the heat of reaction to control vaporization of the reactants in the reactor. A widely practiced form of heat removal is to cool the reactor off-gas in a condenser and return the cold liquid to the reactor, as disclosed in U.S. Pat. No. 4,777,287. Alternatively, the heat of reaction has been removed by circulating a portion of the product-containing liquid at the bottom of the reactor through a heat exchanger and returning it to the reactor, as disclosed in U.S. Pat. No. 4,855,492.

To resolve the two aforementioned problems, the energy created by the heat of reaction has been utilized in the removal of excess water. In a side distillation process, the energy produced from condensation of the reactor off-gas has been used to generate steam, which is then used as part of the heat input to the side distillation column. However, this method does not effectively utilize the heat of reaction. Additional heat sources are generally required to accomplish distillation and additional heat exchangers must be added to the process.

Direct distillation of the reactor off-gas to remove water has conventionally been employed utilizing the heat of reaction. However, process limitations exist. Since the amount of distillate reflux determines the purity of the overhead distillate and the heat input to the distillation process determines the amount of reflux which the process can accommodate, the heat of reaction fixes both the amount of reflux and the purity of the overhead distillate. The heat of reaction alone is generally insufficient to obtain a desirable overhead purity which minimizes solvent loss. Therefore, direct distillation requires additional heat input.

Another effective method of water removal is by azeotropic distillation. U.S. Pat. No. 3,402,184 discloses reactor oxidation vapors being sent directly to an azeotropic distillation column in which benzene is the entraining medium. U.S. Pat. No. 4,250,330 discloses condensed solvent being sent to an isobutyl-acetate azeotropic distillation process. These methods, however, typically require expensive distillation equipment and additional heat exchange equipment. The process is more complicated and expensive since the entraining medium must be purchased, handled, recovered and replenished due to loss and degradation.

Thus, there exists a need for a method to remove the excess water generated from the reaction by effectively using the heat from the energy of oxidation without requiring additional heat input or equipment while also minimizing solvent loss.

SUMMARY OF THE INVENTION

The present invention provides for the effective utilization of the heat of reaction in the process of removing excess water generated from the reaction while minimizing solvent loss. A distilled waste water of low solvent content is produced and the reactor water level is sufficiently maintained to allow for optimal production rates and product quality. These and other advantages are afforded by carrying out the oxidation of an alkyl aromatic hydrocarbon in a columnar reactor wherein the reactor off-gas is fed directly into a water removal column. A portion of the bottoms liquid from the water removal column comprising partially dewatered solvent is sprayed as reflux into the reactor through one or more spray nozzles. The spray reflux enters the reactor above the phase separation of the gas/liquid reaction mixture. A portion of distilled condensed water generated from the water vapor at the top of the water removal column is returned as reflux to the water removal column.

Our invention thus provides a method for the continuous production of an aromatic polycarboxylic acid in a pressurized oxidation reactor by liquid-phase, exothermic oxidation of an alkyl aromatic hydrocarbon with an oxygen-containing gas in the presence of an oxidation catalyst and aqueous, $C_2$–$C_6$ aliphatic, monocarboxylic acid solvent which comprises the steps of:

(1) continuously feeding to a reactor alkyl aromatic hydrocarbon, aqueous, monocarboxylic acid solvent having oxidation catalyst dissolved therein, and an oxygen containing gas;

(2) continuously removing from the lower portion of the reactor product-containing liquid comprising aromatic polycarboxylic acid and the aqueous, monocarboxylic solvent having the oxidation catalyst dissolved therein;

(3) continuously removing from the upper portion of the reactor and feeding directly into a lower portion of a water removal column reactor off-gas comprising oxygen-depleted gas and vaporized aqueous, mono-carboxylic acid solvent;

(4) continuously removing from the lower portion of the water removal column a bottoms liquid containing partially de-watered monocarboxylic acid solvent;

(5) returning to the reactor at least a portion of the bottoms liquid obtained in step (4) in the form of a spray above the phase separation of the gas/liquid contents of the reactor;

(6) continuously removing from the water removal column overhead aqueous vapors having minimal monocarboxylic acid solvent therein;

(7) condensing the aqueous vapors into a distillate product; and (8) returning to the fractionating zone of the water removal column at least a portion of the distillate product obtained in step (7).

BRIEF DESCRIPTION OF THE DRAWING

The accompanying

DETAILED DESCRIPTION OF THE INVENTION

Figure 1:
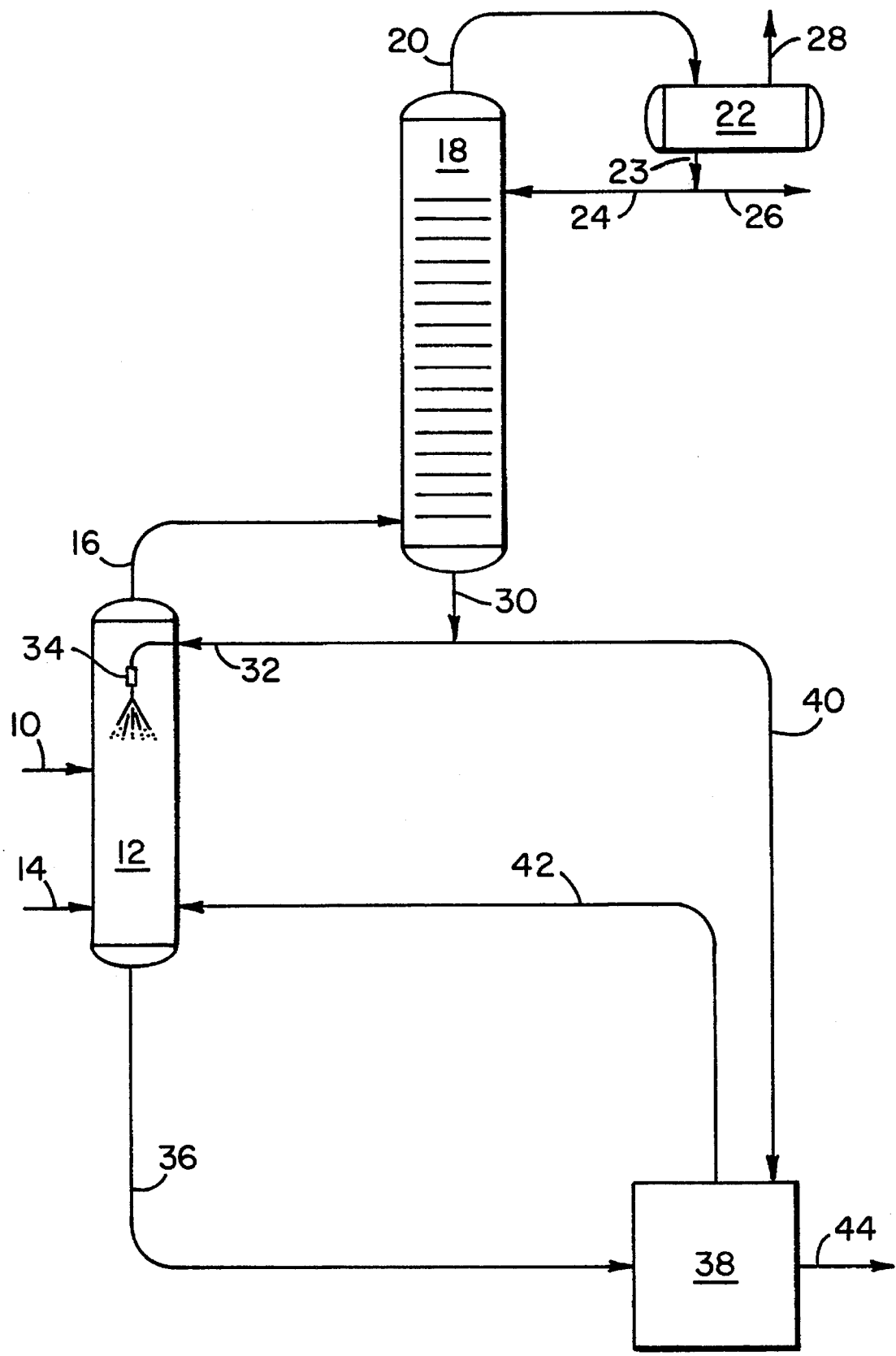
FIG. 1 is a process flow diagram illustrating a system embodying the principles of the method of the present invention.

While the present invention is susceptible to embodiment in various forms, there is shown in the accompanying FIG. 1 and hereinafter described in detail a preferred embodiment of the invention. The present disclosure is to be considered as an exemplification of the invention without limitation to the specific embodiment illustrated.

Referring to the accompanying FIG. 1, reactor feed mixture is introduced via conduit 10 into oxidation reactor 12. The reactor feed mixture comprises an alkyl aromatic hydrocarbon, an aqueous, $C_2$ to $C_6$ monocarboxylic aliphatic acid solvent, and a suitable oxidation catalyst which is typically dissolved in the solvent. The aliphatic, carboxylic acid solvent feed typically contains up to about 10 weight percent water. If desired, the alkyl aromatic compound, and/or aliphatic acid solvent containing catalyst components may be fed to reactor 12 at a plurality of points along the side of the reactor. An oxygen-containing gas under pressure is introduced near the bottom of the reactor 12 via conduit 14. The preferred oxygen-containing gas is air. The flow rate of the oxygen-containing gas to reactor 12 is controlled to maintain between about 2 and 9 volume percent oxygen (calculated on a dry, solvent free basis) in the off-gas which exits the reactor via conduit 16. The reactants in reactor 12 are maintained at an elevated pressure sufficient to maintain a contained, volatilizable reaction medium substantially in the liquid state at the reaction temperature.

Reactor 12 is a columnar, pressurized, oxidation vessel wherein liquid-phase exothermic oxidation of the alkyl aromatic hydrocarbon by the oxygen-containing gas takes place in the presence of the oxidation catalyst. The reaction medium contained by reactor 12 thus comprises the oxygen-containing gas, the alkyl aromatic hydrocarbon that is to be oxidized to an aromatic carboxylic acid product, the catalyst, and the aqueous, $C_2$ to $C_6$ monocarboxylic aliphatic acid solvent. Utilizing the method of the present invention, the amount of water within the reactor does not generally exceed about 8 to 10 weight percent based on the weight of the water and the aliphatic, carboxylic acid.

During the course of the oxidation reaction, exothermic heat of reaction and water generated by the oxidation of the alkyl aromatic compound are removed from the reactor 12 by vaporization of a portion of the liquid reaction medium. These vapors, known as reactor off-gas, comprise the aqueous solvent at about five (5) to thirty (30) weight percent water and oxygen-depleted process gas containing minor amounts of decomposition products including catalyst residue. The reactor off-gas passes upwardly through the reactor 12 and is introduced via conduit 16 into a lower portion of a water removal column 18 for distillation. The water removal column may be a distillation column having a fractionating zone of either a plurality of trays or a suitable packing for effecting mass transfer and may have twenty-five (25) or more equilibrium stages and a refluxed top section.

Overhead aqueous vapors exit the upper portion of the water removal column 18 through conduit 20 into a condenser 22. The composition of the condensible components of the aqueous vapors collected in the condenser 22, known as the distillate, is above about ninety-nine (99) percent water. A portion of the distillate is returned as reflux to the fractionating zone of the water removal column 18 via conduits 23 and 4. The other portion of the distillate is removed for disposal via conduits 23 and 26. The reflux ratio by weight ranges from four (4) to seven (7) parts reflux distillate to one (1) part disposal distillate. An additional stream of water (not shown) containing minor amounts of acid solvent generated from other water processes such as pump seals, vent scrubbers and water washing may be fed to the water removal column 18. The non-condensible components are vented via conduit 28 or may be transported to a pollution control device for further treatment if desired.

A distilled bottoms liquid containing partially dewatered monocarboxylic aliphatic acid solvent of about four (4) to twelve (12) weight percent water exits the lower portion of the water removal column 18 via conduit 30. A portion of the partially de-watered solvent is recycled directly to the reactor 12 via conduit 32. This amount ranges from ten (10) to one hundred (100) percent depending on the amount of partially de-watered solvent utilized for washing catalyst from a product-containing liquid of the reactor 12 as described below. In accordance with our invention, the partially de-watered solvent is fed to the reactor 12 by means of spray head 34 located below exit conduit 16 and above the phase separation of the gas/liquid contents of the reactor 12. The spray head 34 is designed to distribute the partially de-watered solvent in a finely divided form, e.g., droplets, over a substantial portion, preferably over all, of the surface of the phase separation of the gas/liquid reaction mixture. The particular means employed to feed the partially de-watered solvent in the form of a spray to the reactor is not critical so long as it provides liquid-gas contact at the top of the reactor. Thus, the spray may be created by means of a single spray head as shown in the FIG. 1 or by a plurality of spray nozzles.

The reactor 12 continuously produces a product-containing liquid of an aromatic carboxylic acid that is continuously withdrawn as a slurry in the aqueous, monocarboxylic aliphatic acid solvent, which also contains dissolved catalyst. The product-containing liquid exits the bottom portion of the reactor 12 and is conveyed via conduit 36 to a suitable solid/liquid separation system 38. A second portion of the partially de-watered solvent as supplied from the bottom of the water removal column via conduits 30 and 40 is used in the separation system 38 for washing catalyst from the product-containing liquid. The liquid phase recovered from separation system 38 comprising solvent with dissolved catalyst components and water is recycled to the bottom portion of reactor 12 via conduit 42. The solids phase contains the product of the process, aromatic carboxylic acid compound, and is transported for recovery via conduit 44.

In distillation processes, high purity distillate products are typically desired. The purity or richness of the distillate is determined by the amount of reflux, i.e. higher reflux ratio, richer distillate. However, if the reflux is increased, the amount of heat to operate the distillation process must also be increased. Thus, the amount of reflux that the distillation process can accommodate, as well as the purity of the distillate, is limited by the heat of reaction unless additional heat input is provided. With the improvement of the present invention, that is the introduction into the reactor of a spray of partially de-watered solvent obtained as the bottoms liquid from the water removal column, the efficiency of the distillation process is increased over conventional distillation processes to provide a distillate of above ninety-nine (99) percent water accomplished utilizing only the exothermic heat of reaction. Such level of distillate purity is generally not attainable without additional heat sources which also increase cost. It is the interaction between the water removal column and the reactor through the spray and reactor off-gas that causes the reactor to act as a reboiler for the water removal column, thus eliminating the need for additional heat input to effect distillation.

The spray effects a higher concentration of water and a lower concentration of aliphatic acid solvent in the reactor off-gas due to the vaporization of the water in the spray. The atomized water from spraying readily vaporizes into the reactor off-gas limiting any increase in the water concentration of the reaction medium, which must be maintained at a certain level for the reaction to proceed. By lowering the concentration of solvent fed to the water removal column, less energy is needed for separation and the reflux ratio can be increased without additional heat input to effect a richer concentration of water in the distillate. The heat of reaction now provides the necessary energy to result in the water rich distillate. Thus, the operating efficiency of the water removal system is increased since more water generated from the oxidation reaction may exit the process as distillate through conduit 26 with minimal solvent loss at no additional cost related to increased heat input. The valuable aliphatic acid solvent is confined to the process in the bottoms liquid of the water removal column rather than rejected to waste.

Furthermore, the spray knocks down entrained solids and vaporized material which produce solids upon cooling, thereby preventing the fouling or plugging of process equipment such as lines, condensers and distillation columns. It also decreases the concentration of bromine-containing compounds in vapor conduit 16 which decreases the rate of corrosion of process equipment. The spray also permits the use of higher pressures and higher levels of the gas/liquid reaction mixture within the reactor which increase the overall efficiency of the process.

Examples of suitable alkyl aromatic hydrocarbons useful as reactor feed-mixture components or ingredients in the method of the present invention and their respective aromatic carboxylic acid products are as follows:

| hydrocarbon | acid |
| --- | --- |
| toluene | benzoic acid |
| o-xylene | orthophthalic acid |
| m-xylene | isophthalic acid (IPA) |
| p-xylene | terephthalic acid (TPA) |
| 1,2,3-trimethyl benzene | hemimellitic acid |
| 1,2,4-trimethyl benzene | trimellitic acid |
| 1,2,5-trimethyl benzene | trimesic acid |
| 2,6- and 2,7-dimethyl naphthalene | 2,6- and 2,7-naphthalene dicarboxylic acids. |

The method is particularly well suited for the production of TPA, IPA, trimellitic acid, trimesic acid and the naphthalenedicarboxylic acids.

Suitable aqueous aliphatic acid solvents useful in the method of this invention are those that are readily volatilizable at the reaction temperatures. Among such solvents are aqueous solutions of $C_2$ to $C_6$ mono-carboxylic acids, e.g., acetic acid, propionic acid, n-butyric acid, isobutyric acid, n-valeric acid, trimethylacetic acid, caproic acid, and mixtures thereof. Preferably, the volatilizable monocarboxylic aliphatic acid solvent is acetic acid.

The catalyst systems which may be employed in the oxidation process include any catalyst system conventionally used for liquid-phase oxidation of an alkyl aromatic hydrocarbon. A suitable catalyst system may include a mixture of cobalt, manganese and bromine compounds or complexes, soluble in the particular volatilizable aqueous solvent employed.

In a specific example of the improved process of the present invention, p-xylene at a rate of 1000 parts by weight per hour was fed to the reactor 12 and oxidized to produce medium purity TPA at a rate of 1600 parts by weight per hour. The reactor used was a vertical bubble column having a height:diameter ratio of 13.3. All amounts of material were measured in parts by weight.

Aqueous acetic acid containing dissolved catalyst was fed at the rate of about 30 parts per hour and p-xylene was fed at the rate of about 1000 parts per hour via conduit 10 to the reactor 12. Air with 0.5% water was fed via conduit 14 at a rate of about 4900 parts per hour air. The oxidation reaction medium filled approximately 85% of the volume of the reactor. The temperature of the vigorously mixed reaction medium was about 140° to 160° C. and the pressure was controlled at about 75 psia. Typical operating temperatures and pressures range respectively from about 120° to 180° C. and from about 50 to 175 psia. TPA slurried in acetic acid was removed from the reactor via conduit 36 at the rate of about 1600 parts per hour.

A reactor off-gas stream comprising oxygen--depleted air, acetic acid and water was removed continuously via a port located at the top of the reactor and transported via conduit 16 to the lower portion of the water removal column 18. The water concentration in conduit 16 was about 9.4% by weight based on condensibles. A bottom liquid of partially de-watered acetic acid with a water concentration of about 6% by weight was removed via conduit 30 from the water removal column 18 at a rate of about 15,800 parts per hour acetic acid. A portion of the partially de-watered solvent was fed to the reactor via conduit 32 and spray head 34 at a rate of about 9000 parts per hour acetic acid. The remainder of the partially de-watered solvent was fed to the separation system 38 via conduit 40.

Overhead aqueous vapors continuously exited the upper portion of the water removal column through conduit 20 into a condenser 22. The condensible liquid components comprising 99.5% by weight water and 0.5% by weight acetic acid exited the condenser 22 through conduit 23 at a rate of about 3600 parts per hour. A portion of the condensate was refluxed to the water removal column 18 via conduit 24 at a rate of about 3200 parts per hour. The remainder of the condensate exited the system via conduit 26 at a rate of about 470 parts per hour. The resulting reflux ratio of the water removal column was about 6.8. The non-condensibles exited the condenser 22 via conduit 28 at a rate of about 4100 parts per hour.

The invention has been described in detail with particular reference to preferred embodiments thereof, but it will be understood that variations and modifications can be effected within the spirit and scope of the invention.

We claim:

1. A process for the continuous production of an aromatic polycarboxylic acid in a pressurized oxidation reactor by liquid-phase, exothermic oxidation of an alkyl aromatic hydrocarbon with an oxygen-containing gas in the presence of an oxidation catalyst and aqueous, $C_2$–$C_6$ aliphatic, monocarboxlyic acid solvent which comprises the steps of:

(1) continuously feeding to a reactor alkyl aromatic hydrocarbon, aqueous, monocarboxylic acid solvent having oxidation catalyst dissolved therein and oxygen containing gas;

(2) continuously removing from the lower portion of the reactor product-containing liquid comprising aromatic polycarboxylic acid and the aqueous, monocarboxylic solvent having the oxidation catalyst dissolved therein;

(3) continuously removing from the upper portion of the reactor and feeding directly into a lower portion of a water removal column reactor off-gas comprising oxygen-depleted gas and vaporized aqueous, monocarboxylic acid solvent;

(4) continuously removing from the lower portion of the water removal column a bottoms liquid containing partially de-watered monocarboxylic acid solvent;

(5) returning to the reactor at least a portion of the bottoms liquid obtained in step (4) in the form of a spray above the phase separation of the gas/liquid contents of the reactor;

(6) continuously removing from the water removal column overhead aqueous vapors having minimal monocarboxylic acid solvent therein;

(7) condensing the aqueous vapors into a distillate product; and (8) returning to a fractionating zone of the water removal column at least a portion of the distillate product obtained in step (7).

2. The process according to claim 1 wherein the monocarboxylic acid solvent is acetic acid, alkyl aromatic hydrocarbon is p-xylene, and the aromatic polycarboxylic acid is terephthalic acid.

3. The process according to claim 1 wherein condensing the aqueous vapors results in the distillate product comprising above about 99 percent water.

4. A continuous process for producing an aromatic polycarboxylic acid product from an exothermic reaction, comprising:

combining in a pressurized oxidation reactor alkyl aromatic hydrocarbon, oxidation catalyst, aqueous solvent of $C_2$–$C_6$ aliphatic, monocarboxlyic acid and oxygen-containing gas to produce a reaction mixture having a vapor phase and a product-containing liquid phase;

removing heat and water generated by exothermic reaction from the vapor phase by withdrawing a portion of the vapors from the reactor and passing the withdrawn vapors directly into a bottom portion of a water removal column;

generating from the water removal column a bottoms liquid containing partially de-watered solvent and overhead aqueous vapors having minimal solvent content therein;

recycling to the reactor a portion of the bottoms liquid in the form of a spray above the phase separation of the gas/liquid contents of the reactor, whereby the water content of the vapors from the reactor is enriched; and condensing the overhead aqueous vapors from the water removal column and refluxing a portion of the condensate into a fractionating zone of the water removal column and disposing of the other portion of the condensate, whereby the water removal column is operated utilizing the heat generated by the exothermic reaction to produce the condensate having minimal solvent content.

5. The process according to claim 4 wherein the condensate has a water content of above about 99 percent and a solvent content of below about one percent.

6. Method for the continuous production of terephthalic acid in a pressurized oxidation reactor by liquid-phase, exothermic oxidation of p-xylene with oxygen-containing gas in the presence of oxidation catalyst and aqueous acetic acid which comprises the steps of:

(1) continuously feeding to a reactor p-xylene, aqueous, acetic acid having oxidation catalyst dissolved therein and air;

(2) continuously removing from the lower portion of the reactor product-containing liquid comprising terephthalic acid and aqueous acetic acid having the oxidation catalyst dissolved therein;

(3) continuously removing from the upper portion of the reactor and feeding directly into a lower portion of a water removal column reactor off-gas comprising oxygen-depleted gas and vaporized aqueous, acetic acid;

(4) continuously removing from the lower portion of the water removal column a bottoms liquid containing partially de-watered acetic acid;

(5) returning to the reactor 10 to 100% of the of the bottoms liquid obtained in step (4) in the form of a spray above the phase separation of the gas/liquid contents of the reactor;

(6) continuously removing from the water removal column overhead aqueous vapors having minimal acetic acid therein;

(7) condensing the overhead aqueous vapors into a distillate product; and (8) returning to the fractionating zone of the water removal column at least a portion of the distillate product obtained in step (7).

* * * * *